(12) United States Patent
Martineau

(10) Patent No.: US 11,877,870 B2
(45) Date of Patent: Jan. 23, 2024

(54) SYSTEMS, METHODS AND APPARATUS FOR PREVENTION OF INJURY

(71) Applicant: Consultation Semperform Inc., Westmount (CA)

(72) Inventor: Paul Andre Martineau, Westmount (CA)

(73) Assignee: Consultation Semperform Inc, Westmount (CA)

( * ) Notice: Subject to any disclaimer, the term of this patent is extended or adjusted under 35 U.S.C. 154(b) by 1096 days.

(21) Appl. No.: 16/532,450

(22) Filed: Aug. 5, 2019

(65) Prior Publication Data

US 2021/0038167 A1 Feb. 11, 2021

(51) Int. Cl.
*A61B 5/00* (2006.01)
*A61B 5/11* (2006.01)

(52) U.S. Cl.
CPC .......... *A61B 5/7282* (2013.01); *A61B 5/0077* (2013.01); *A61B 5/112* (2013.01); *A61B 5/1121* (2013.01); *A61B 5/1128* (2013.01); *A61B 5/4585* (2013.01); *A61B 5/7275* (2013.01); *A61B 2503/10* (2013.01); *A61B 2576/02* (2013.01)

(58) Field of Classification Search
None
See application file for complete search history.

(56) References Cited

U.S. PATENT DOCUMENTS

| 9,161,708 | B2 | 10/2015 | Elliott et al. | |
| 11,210,834 | B1* | 12/2021 | Chamdani | G06T 13/40 |
| 2011/0208444 | A1 | 8/2011 | Solinsky | |
| 2011/0270135 | A1 | 11/2011 | Dooley et al. | |
| 2012/0029345 | A1 | 2/2012 | Mahfouz | |
| 2013/0137962 | A1 | 5/2013 | Urish | |
| 2013/0223707 | A1* | 8/2013 | Stephenson | A61B 5/1124 382/128 |
| 2013/0324888 | A1 | 12/2013 | Solinsky | |
| 2014/0228712 | A1 | 8/2014 | Elliott et al. | |
| 2014/0228985 | A1 | 8/2014 | Elliott et al. | |
| 2015/0005910 | A1* | 1/2015 | Ishii | G06V 40/23 700/91 |
| 2015/0139502 | A1* | 5/2015 | Holohan | G06T 7/251 382/107 |
| 2015/0287338 | A1 | 10/2015 | Wells et al. | |
| 2016/0129343 | A1* | 5/2016 | Domansky | A61B 5/486 463/7 |
| 2016/0220867 | A1* | 8/2016 | Flaherty | G16H 20/30 |

(Continued)

OTHER PUBLICATIONS

Arneja, Validity of the KT-1000 Knee Alignment Arthometer, Journal of Orthopaedic Surgery 2009, 17(1): 77-9, Joint Preservation Centre of British Columbia, Univ. of British Columbia Hospital, 2nd Floor, Unit 2C, 2211 Westbrook Mall, Vancouver, BC, Canada V6T2B5.

(Continued)

*Primary Examiner* — Benjamin S Melhus

(74) *Attorney, Agent, or Firm* — Michael G. Smith, Esq.

(57) ABSTRACT

Systems, methods and apparatus are provided through which in some implementations, a system calculates a potential for ACL injury of a subject using skeletal tracking and calculating joint angles at different time points from the motion, angle of the knee joint, jumping/landing mechanics and/or balance of the subject.

14 Claims, 6 Drawing Sheets

(56) References Cited

U.S. PATENT DOCUMENTS

| | | | |
|---|---|---|---|
| 2017/0177930 A1* | 6/2017 | Holohan | G06T 7/251 |
| 2017/0243346 A1* | 8/2017 | Hall | G06V 40/23 |
| 2017/0278419 A1 | 9/2017 | Wells et al. | |
| 2018/0020954 A1 | 1/2018 | Lillie et al. | |
| 2018/0125395 A1* | 5/2018 | Myer | A61B 5/742 |
| 2018/0184947 A1* | 7/2018 | Richards | A61B 5/1071 |
| 2018/0289324 A1* | 10/2018 | Kianifar | A61B 5/1121 |
| 2018/0304118 A1 | 10/2018 | French | |
| 2019/0172585 A1* | 6/2019 | Mazumder | G06T 17/00 |
| 2019/0175121 A1* | 6/2019 | Hall | G06V 40/23 |
| 2020/0054931 A1* | 2/2020 | Martin | A61B 5/486 |
| 2020/0085348 A1* | 3/2020 | Lillie | A61B 5/4533 |
| 2020/0147451 A1* | 5/2020 | Frank | A61B 5/024 |
| 2020/0275881 A1* | 9/2020 | Sawacha | A61B 5/1036 |
| 2020/0285844 A1* | 9/2020 | Holohan | G06V 40/23 |
| 2022/0101588 A1* | 3/2022 | Garofalo | G06F 3/017 |

OTHER PUBLICATIONS

Campbell et al., Neuromuscular Training Programs Can Decrease Anterior Cruciate Ligament Injuries in Youth Soccer Players, Clin J Sport Med 2014; 24:263-267, Canadian Academy of Sport and Exercise Medicine, www.cjsportmed.com.

Dallinga et al., Which Screening Tools Can Predict Injury to the Lower Extremities in Team Sports?, Sports Med 2012; 42 (9): 791-815, Springer International Publishing AG.

Gornitzky et al., Sport-Specific Yearly Risk and Incidence of Anterior Cruciate Ligament Tears in High School Athletes, The American Journal of Sports Medicine (AJSM) vol. 44, No. 10, 2016, DOI: 10.1177/0363546515617742.

Hewett et al., Multicenter Trial of Motion Analysis for Injury Risk Prediction: Lessons Learned from Prospective Longitudinal Large Cohort Combined Biomechanical-epidemiological Studies, Brazilian Journal of Physical Therapy vol. 19 No. 5, Sep./Oct. 2015.

Ireland, The Female ACL: why is it more prone to injury?, Orthop Clin N Am 33 (2002) 637-651, Kentucky Sports Medicine, 601 Perimeter Dr., Lexington, KY 40517.

Sigimoto et al., Dosage Effects of Neuromuscular Training Intervention to Reduce Anterior Cruciate Ligament Injuries in Female Athletes: Meta- and Sub-Group Analyses, Sports Med (2014) 44:551-562, DOI 10.1007/s40279-013-0135-9, Dec. 27, 2013, Springer International Publishing Switzerland 2013.

* cited by examiner

SOLID-STATE IMAGE TRANSDUCER 500

SYSTEMS, METHODS AND APPARATUS FOR PREVENTION OF INJURY

FIELD

This disclosure relates generally to medical image analysis, injury prevention, and more particularly to anterior cruciate ligament (ACL) ligament analysis.

BACKGROUND

The anterior cruciate ligament (ACL) ligament is one of a pair of cruciate ligaments in the human knee. The two ligaments are also called cruciform ligaments, as they are arranged in a crossed formation. In the quadruped stifle joint, based on its anatomical position, the ACL ligament is also referred to as the cranial cruciate ligament.

ACL injuries (such as tears) are frequent injuries, making ACL reconstruction one of the most commonly performed orthopedic surgeries. Despite significant advances in surgical techniques over the years, ACL reconstruction remains fraught with frequent complications like graft rupture and instability that lead to clinical failure, and ultimately osteoarthritis. Risk factors that have been associated with ACL injury include the size of the femoral notch, the diameter of the ACL, the mechanical axis of the lower extremities and other specific anatomical features. Although ACL tears can occur in many sports, ACL tears are exceedingly prevalent in pivoting sports such as soccer. Female athletes are particularly prone to ACL, in fact, female athletes tear their ACL at least two and up to eight times more frequently than male athletes. Multiple factors have been associated with the higher risk of ACL injury in women athletes, such as the size of the femoral notch, the diameter of the ACL, the mechanical axis of the lower extremities, hormonal status and increased knee laxity. Many of these factors are not modifiable, other factors such as core stability, quadriceps dominance and jumping/landing mechanics in women are different than in men and thought to be important risk factors for ACL injuries. These differences in neuromuscular coordination put the ACL under conditions of increased strain in female athletes. Neuromuscular training programs have been shown to decrease injury rates in populations of female athletes. However, the adoption of these programs is far from uniform nor widespread. One of the current solutions to study and prevent ACL injuries are expensive gait motion analysis laboratories, which place many reflective markers on patients, record video and then perform analysis which can take upward of 2 hours per patient. These motion analysis laboratories are extremely expensive. The use of these motion analysis systems has shown that jumping dynamics can reliably predict risk of knee injury, but such systems are not portable, and are for the most part are only available in academic institutions for well-equipped research purposes and not for population general use.

BRIEF DESCRIPTION

The above-mentioned shortcomings, disadvantages and problems are addressed herein, which will be understood by reading and studying the following specification.

Given the sheer amount of ACL injuries, the identifiable neuromuscular risk factors and the vulnerability, in particular, of female athletes to this devastating injury with long term consequences, I have developed injury prevention technique and system software that are powerful and easy to use and adopt using commercially available motion capture hardware that is readily available and soon to be found in most smartphones. The system software can serve as a screening tool for therapists, coaches, medical professionals, even parents to identify athletes with specific neuromuscular imbalances predisposing them to ACL injury. The system software recognizes and flags athletes at high risk of ACL tears. The application alerts the athletes and those involved in his/her success to the need for participation in a corrective exercise program/neuromuscular training program. The system software also assesses a successful correction of the risky neuromuscular coordination. The system software also guides return to play decisions particularly in the context of recovering from ACL reconstruction surgery.

I have pioneered a portable, low-cost and user-friendly solution that can provide a useful screening tool for athletes at risk of injury and that can be adopted by medical professionals but also by coaches, parents and athletes themselves, for widespread ACL injury prevention at the global level.

In one aspect, a system calculates an injury risk score for a subject using skeletal tracking or pose recognition and calculating joint angles at different time points from the motion, angle of the knee joint, jumping/landing mechanics, balance of the subject and if the score is over a predetermined threshold, then flags the subject as being "at risk". Additional variables such as biological gender of the subject (male vs female), sport(s) played by the subject, and/or previous injury(ies) of the subject; can also be added.

In another aspect, a computer-based system determines a potential injury to a knee anterior cruciate ligament of a subject, the computer-based system includes a motion sensing input device and a computer having a processor, a memory and input/output capability, the memory being configured to perform skeletal tracking and calculating joint angles at different time points and being configured to analyze the motion of the subject, angle of the knee joint of the subject, jumping and landing mechanics of the subject and balance of the subject in reference to the skeletal tracking and calculating joint angles at different time points, and to determine the potential injury to the knee anterior cruciate ligament of the subject.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION

In the following detailed description, reference is made to the accompanying drawings that form a part hereof, and in which is shown by way of illustration specific implementations which may be practiced. These implementations are described in sufficient detail to enable those skilled in the art to practice the imamplementations, and it is to be understood that other implementations may be utilized and that logical, mechanical, electrical and other changes may be made without departing from the scope of the implementations. The following detailed description is, therefore, not to be taken in a limiting sense.

The detailed description is divided into five sections. In the first section, a system level overview is described. In the second section, apparatus of implementations are described. In the third section, implementations of methods are described. In the fourth section, a hardware and the operating environment in conjunction with which implementations may be practiced are described. Finally, in the fifth section, a conclusion of the detailed description is provided.

Figure 1:
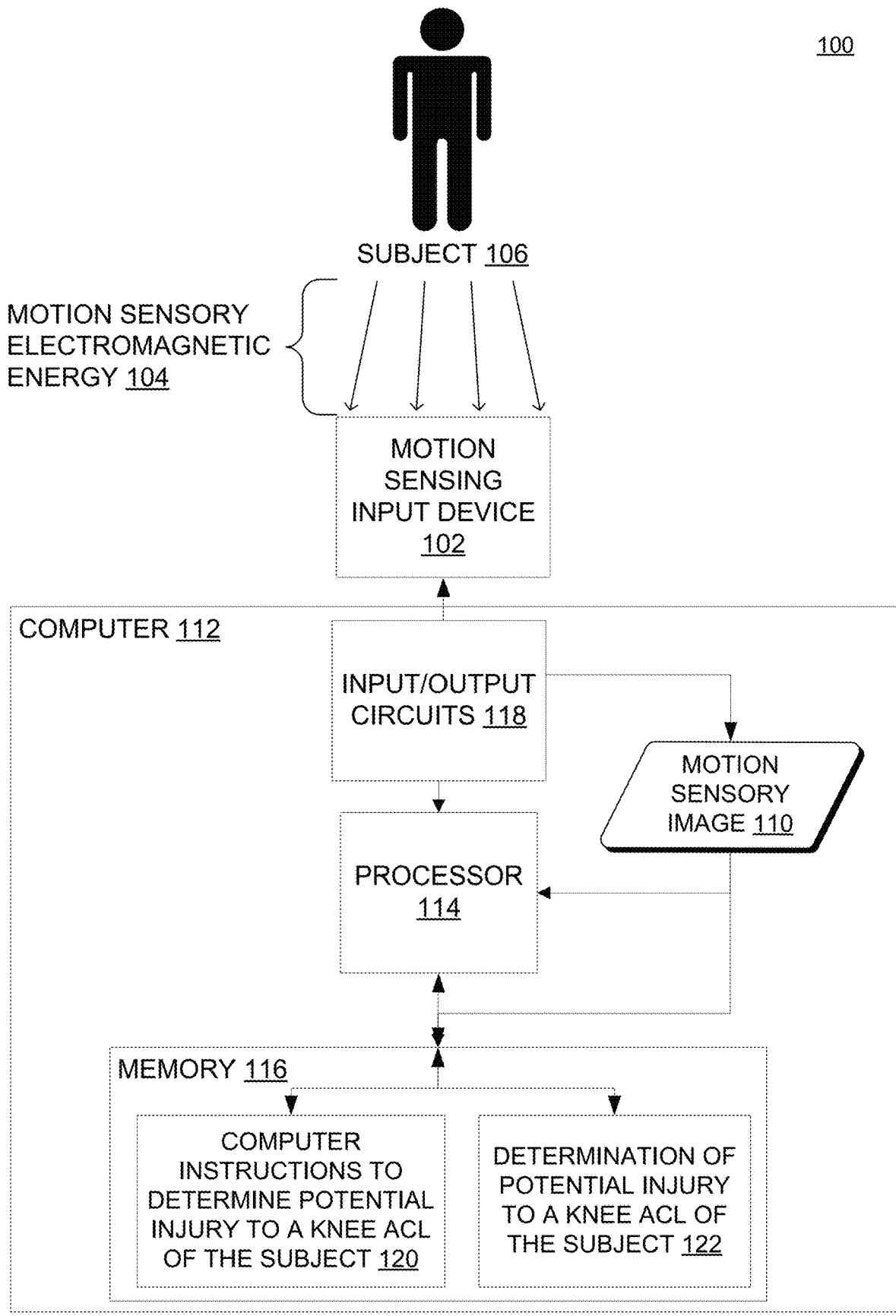
FIG. 1 is a block diagram of an anterior cruciate ligament injury screening system, according to an implementation.
Figure 2:
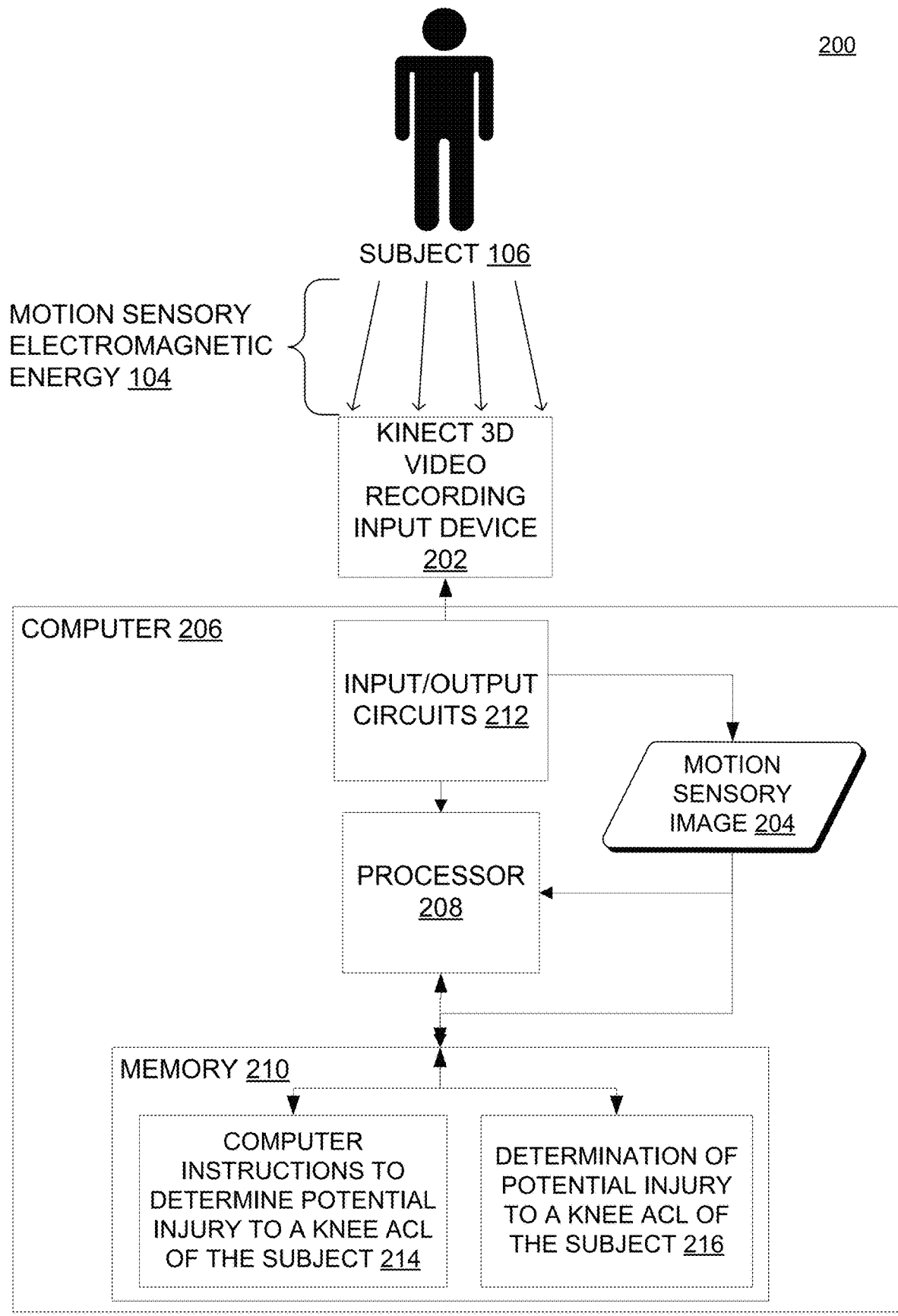
FIG. 2 is a block diagram of an anterior cruciate ligament injury screening system, according to an implementation that includes a Microsoft Kinect for Xbox One.
Figure 3:
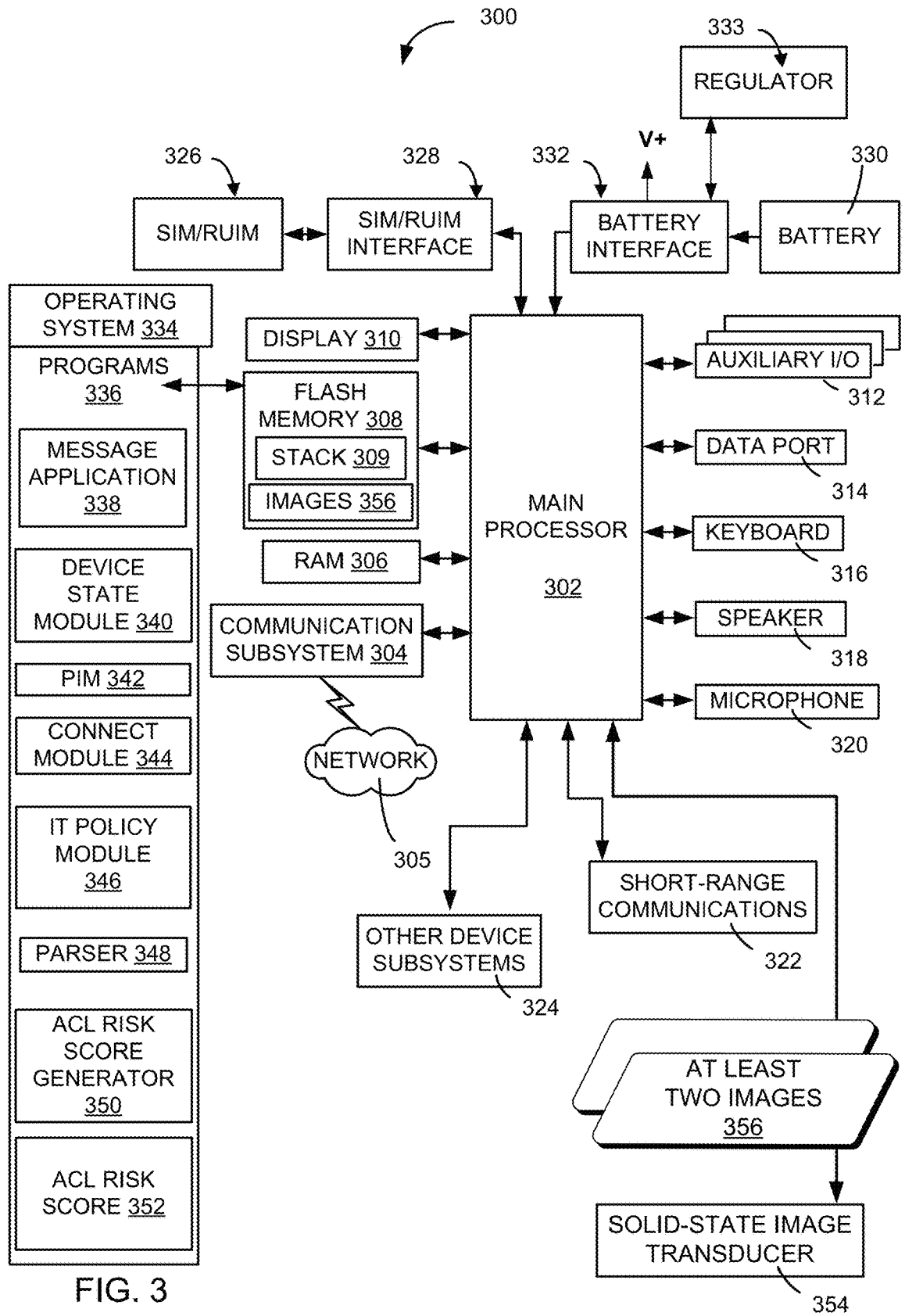
FIG. 3 is a block diagram of a hand-held imaging system, according to an smartphone implementation.
Figure 4:
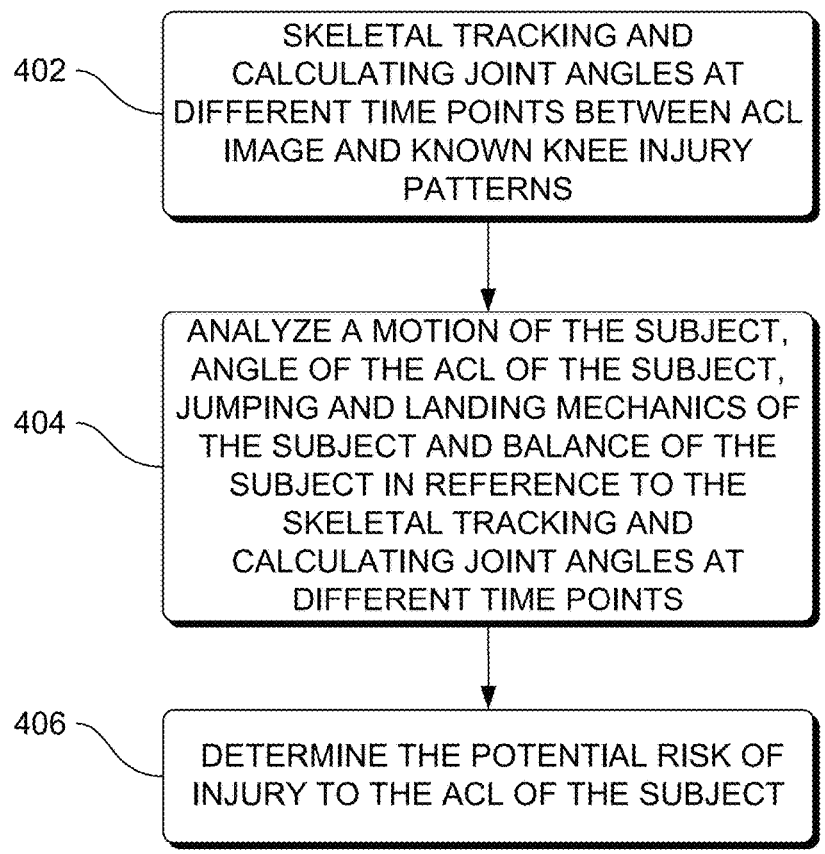
FIG. 4 is a flowchart of a method to determine potential injury to a ACL of a subject (expressed as a ACL risk score) from motion sensory images of a knee of the subject, according to an implementation.
Figure 6:
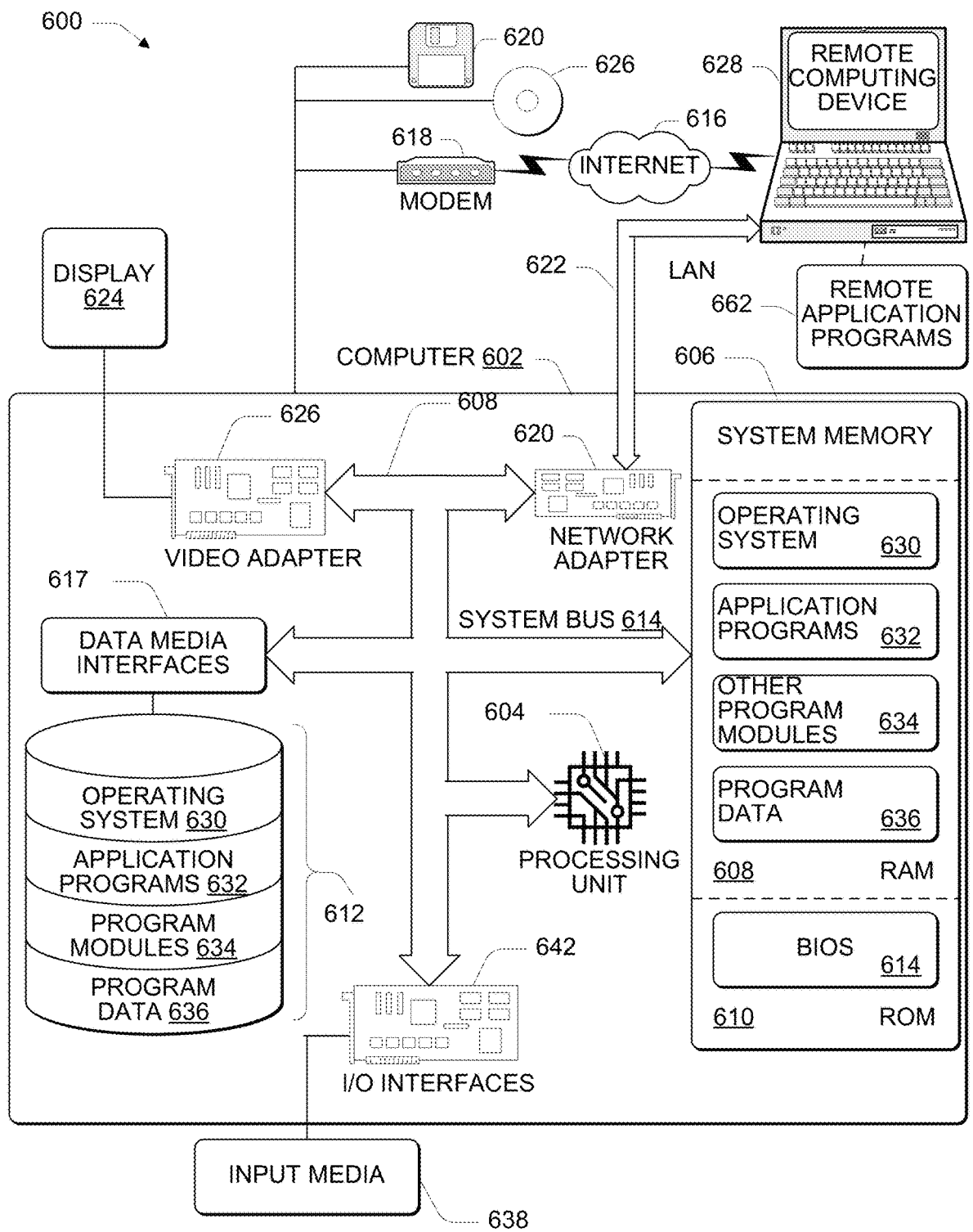
FIG. 6 is a block diagram of a hardware and operating environment in which different implementations can be practiced.

The system 100 in FIG. 1, the system 200 in FIG. 2, the hand-held imaging system 300 in FIG. 3, the method 400 in FIG. 4 and the hardware and operating environment 600 in FIG. 6 do not include a motion profile that further includes ranges of node angle value, do not comprise ranges of node angle value in a motion profile, do not comprise a motion profile that has ranges of node angle value or that has displacement experienced for one or more exercises, do not comprise a database of previously recorded motion profiles, and do not determine a rehab/treatment schedule.

System Level Overview

FIG. 1 is a block diagram of an anterior cruciate ligament injury screening system 100, according to an implementation. System 100 provides a determination of potential of injury to a knee anterior cruciate ligament of a subject.

System 100 includes a motion sensing input device 102 that detects motion sensory electromagnetic energy 104 of a subject 106 and that generates a motion sensory image 110 of the subject 106. In one implementation, the motion sensory image 110 is captured while the subject performs a standardized drop-vertical-jump procedure, a standardized tuck jump procedure or a standardized triple single leg hop procedure, which are commonly utilized in the assessment of knee injury. The motion sensing input device 102 is operably coupled to a computer 112. In some implementations, the motion sensing input device 102 records 4-5 seconds of motion sensory imagery, at 30 hz (roughly 15 frames per second), which is 60-75 frames of useful information.

In some implementations, the motion sensing input device 102 includes an RGB camera, a depth sensor and a microphone array running proprietary software which provide full-body 3D motion capture, facial recognition and voice recognition capabilities. Some implementations of the microphone array of the motion sensing input device 102 enable acoustic source localization and ambient noise suppression. Some implementations of the depth sensor of the motion sensing input device 102 include an infrared laser projector combined with a monochrome CMOS sensor, which captures video data in 3D under any ambient light conditions, in which the sensing range of the depth sensor is adjustable, and the depth sensor can be calibrated based on the duration of the motion sensory capture and the surrounding physical environment, accommodating for the presence of furniture or other obstacles. Some implementations the motion sensing input device 102 provides the motion sensing image 110 of more than one subject 106 in the field of view of the motion sensing input device 102. Some implementations the motion sensing input device 102 outputs video at a frame rate of ≈9 Hz to 30 Hz depending on resolution, in which the default RGB video stream uses 8-bit VGA resolution (640×480 pixels) with a Bayer color filter, using components capable of resolutions up to 1280×1024 (at a lower frame rate) and other colour formats such as UYVY, wherein the monochrome depth sensing video stream is in VGA resolution (640×480 pixels) with 11-bit depth, which provides 2,048 levels of sensitivity, whereby the view is streamed from the IR camera directly (i.e.: before it has been converted into a depth map) as 640×480 video, or 1280×1024 at a lower frame rate; providing a practical ranging limit of 1.2-3.5 m (3.9-11.5 ft) distance. The area required to perform motion by the subject 106 is roughly 6 m2, although the sensor can maintain tracking through an extended range of approximately 0.7-6 m (2.3-19.7 ft). The angular field of view can be 57° horizontally and 43° vertically, while implementations having a motorized pivot is capable of tilting the sensor up to 27° either up or down. In some implementations, a horizontal field of the motion sensing input device 102 at the minimum viewing distance of ≈0.8 m (2.6 ft) is therefore ≈87 cm (34 in), and the vertical field is ≈63 cm (25 in), resulting in a resolution of just over 1.3 mm (0.051 in) per pixel. In some implementations, the microphone array features four microphone capsules and operates with each channel processing 16-bit audio at a sampling rate of 16 kHz.

The computer 112 includes a processor 114, memory 116 and input/output circuits 118. The memory 116 is configured with instructions 120 that the processor 114 can perform for the computer 112 to interact with the motion sensing input device 102 as well as a custom user interface. For example, a numerical analysis module of the instructions 120 identify a number of appropriate frames of recording to perform vector calculus for the coronal and sagittal angles measured during the standardized drop-vertical-jump procedure. The memory is 116 configured with instructions 120 that the processor 114 can perform to calculate motion and the memory 116 is configured with instructions 120 that the processor 114 can perform to analyze motion of the subject 106, angle of the knee joint of the subject, jumping and landing mechanics of the subject 106, balance of the subject 106 in reference to the skeletal tracking and calculating joint angles at different time points, that generates a determination of potential injury 122 to a knee anterior cruciate ligament of a subject 118. Additional variables such as biological gender of the subject 106 (male vs female), sport(s) played by the subject 106, and/or previous injury(ies) of the subject 106 can be input to improve determination of the potential injury to the knee anterior cruciate ligament of the subject 106. The subject 106 has no markers attached to the subject 106.

While the system 100 is not limited to any particular motion sensing input device 102, motion sensory electromagnetic energy 104, subject 106, motion sensory image 110, computer 112, processor 114, memory 116, input/output circuits 118, instructions 120 or determination of potential injury 122 to a knee anterior cruciate ligament of the subject; for sake of clarity, a simplified motion sensing input device 102, motion sensory electromagnetic energy 104, subject 106, motion sensory image 110, computer 112, processor 114, memory 116, input/output circuits 118, instructions 120 and determination of potential injury 122 to a knee anterior cruciate ligament of the subject are described.

Apparatus Implementations

FIG. 2 is a block diagram of an anterior cruciate ligament injury screening system 200, according to an implementation that includes a Microsoft Kinect for Xbox One. System 200 provides a determination of potential injury to a knee anterior cruciate ligament of a subject.

System 200 includes a 3D video recording input device 202 such as the Microsoft Kinect for Xbox One that detects motion sensory electromagnetic energy 104 of a subject 106 and that generates a motion sensory image 204 of the subject 106. In one implementation, the motion sensory image 204 is captured while the subject performs a standardized drop-vertical-jump procedure which is commonly utilized in the assessment of knee injury. The 3D video recording input device 202 is operably coupled to a computer 206. In one implementation, the 3D video recording input device 202 records 4-5 seconds of imagery, at 30 hz (roughly 15 frames per second), which is 60-75 frames of useful information. In other implementations, a Wii Remote™, Wii Remote Plus™, Wii Balance Board™ for the Wii™ and Wii U™, PlayStation Move™, PlayStation Eye™ for the PlayStation 3™ or PlayStation Camera™ for the PlayStation 4™ is used in place of the 3D video recording input device 202.

The computer 206 includes a processor 208, memory 210 and input/output circuits 212. The memory 210 is configured with instructions 214 that the processor 208 can perform to interact with a sensor of the Microsoft Kinect for Xbox One; as well as a custom user interface. The memory 210 is configured with instructions 214 that the processor 208 can perform in a numerical analysis module of the instructions 214 to identify a number of appropriate frames of recording to perform vector calculus for coronal and sagittal angles measured during the standardized drop-vertical-jump procedure; and instructions 214 to analyze motion of the subject 106, angle of the knee joint of the subject, jumping and landing mechanics of the subject 106, balance of the subject 106, in reference to the skeletal tracking and calculating joint angles at different time points, and to determine the potential injury to the knee anterior cruciate ligament of the subject 106, that generates a determination 216 of potential injury to a knee anterior cruciate ligament of the subject 106. Additional variables such as biological gender of the subject 106 (male vs female), sport(s) played by the subject 106, and/or previous injury(ies) of the subject 106; can also be input.

While the system 200 is not limited to any particular Microsoft Kinect for Xbox One, motion sensory electromagnetic energy 104, subject 106, motion sensory image 204, computer 206, a processor 208, memory 210, input/output circuits 212, instructions 214 and determination 216; for sake of clarity, a simplified Microsoft Kinect for Xbox One, motion sensory electromagnetic energy 104, subject 106, motion sensory image 204, computer 206, a processor 208, memory 210, input/output circuits 212, instructions 214 and determination 216 are described.

In the previous section, a system level overview of the operation of an implementation was described. In this section, the particular apparatus of such an implementation are described by reference to a series of diagrams.

FIG. 3 is a block diagram of a hand-held imaging system 300, according to a smartphone implementation. The hand-held imaging system 300 includes a number of modules such as a main processor 302 that controls the overall operation of the hand-held imaging system 300. Communication functions, including data and voice communications, can be performed through a communication subsystem 304. The communication subsystem 304 receives messages from and sends messages to wireless networks 305. In other implementations of the hand-held imaging system 300, the communication subsystem 304 can be configured in accordance with the Global System for Mobile Communication (GSM), General Packet Radio Services (GPRS), Enhanced Data GSM Environment (EDGE), Universal Mobile Telecommunications Service (UMTS), data-centric wireless networks, voice-centric wireless networks, and dual-mode networks that can support both voice and data communications over the same physical base stations. Combined dual-mode networks include, but are not limited to, Code Division Multiple Access (CDMA) or CDMA2000 networks, GSM/GPRS networks (as mentioned above), third-generation (3G) networks like EDGE and UMTS, 4G and 5G. Some other examples of data-centric networks include Mobitex™ and DataTAC™ network communication systems. Examples of other voice-centric data networks include Personal Communication Systems (PCS) networks like GSM and Time Division Multiple Access (TDMA) systems.

The wireless link connecting the communication subsystem 304 with the wireless network 305 represents one or more different Radio Frequency (RF) channels. With newer network protocols, these channels are capable of supporting both circuit switched voice communications and packet switched data communications.

The main processor 302 also interacts with additional subsystems such as a Random Access Memory (RAM) 306, a flash memory 308, a display 310, an auxiliary input/output (I/O) subsystem 312, a data port 314, a keyboard 316, a speaker 318, a microphone 320, short-range communications subsystem 322 and other device subsystems 324. In some implementations, the flash memory 308 includes a hybrid femtocell/Wi-Fi® protocol stack 309. The hybrid femtocell/Wi-Fi® protocol stack 309 supports authentication and authorization between the hand-held imaging system 300 into a shared Wi-Fi® network and both a 3G, 4G or 5G mobile networks.

The hand-held imaging system 300 can transmit and receive communication signals over the wireless network 305 after required network registration or activation procedures have been completed. Network access is associated with a subscriber or user of the hand-held imaging system 300. User identification information can also be programmed into the flash memory 308.

The hand-held imaging system 300 is a battery-powered device and includes a battery interface 332 for receiving one or more batteries 330. In one or more implementations, the battery 330 can be a smart battery with an embedded microprocessor. The battery interface 332 is coupled to a regulator 333, which assists the battery 330 in providing power V+ to the hand-held imaging system 300. Future technologies such as micro fuel cells may provide the power to the hand-held imaging system 300.

The hand-held imaging system 300 also includes an operating system 334 and modules 336 to 350 which are described in more detail below. The operating system 334 and the modules 336 to 350 that are executed by the main processor 302 are typically stored in a persistent nonvolatile medium such as the flash memory 308, which may alternatively be a read-only memory (ROM) or similar storage element (not shown). Those skilled in the art will appreciate that portions of the operating system 334 and the modules 336 to 350, such as specific device applications, or parts thereof, may be temporarily loaded into a volatile store such as the RAM 306. Other modules can also be included.

The subset of modules 336 that control basic device operations, including data and voice communication applications, will normally be installed on the hand-held imaging system 300 during its manufacture. Other modules include a message application 338 that can be any suitable module that allows a user of the hand-held imaging system 300 to transmit and receive electronic messages. Various alternatives exist for the message application 338 as is well known to those skilled in the art. Messages that have been sent or received by the user are typically stored in the flash memory 308 of the hand-held imaging system 300 or some other suitable storage element in the hand-held imaging system 300. In one or more implementations, some of the sent and received messages may be stored remotely from the hand-held imaging system 300 such as in a data store of an associated host system with which the hand-held imaging system 300 communicates.

The modules can further include a device state module 340, a Personal Information Manager (PIM) 342, and other suitable modules (not shown). The device state module 340 provides persistence, i.e. the device state module 340 ensures that important device data is stored in persistent memory, such as the flash memory 308, so that the data is not lost when the hand-held imaging system 300 is turned off or loses power.

The PIM 342 includes functionality for organizing and managing data items of interest to the user, such as, but not limited to, e-mail, contacts, calendar events, voice mails, appointments, and task items. A PIM application has the ability to transmit and receive data items via the wireless network 305. PIM data items may be seamlessly integrated, synchronized, and updated via the wireless network 305 with the hand-held imaging system 300 subscriber's corresponding data items stored and/or associated with a host computer system. This functionality creates a mirrored host computer on the hand-held imaging system 300 with respect to such items.

The hand-held imaging system 300 also includes a connect module 344, and an IT policy module 346. The connect module 344 implements the communication protocols that are required for the hand-held imaging system 300 to communicate with the wireless infrastructure and any host system, such as an enterprise system, with which the hand-held imaging system 300 is authorized to interface.

The connect module 344 includes a set of APIs that can be integrated with the hand-held imaging system 300 to allow the hand-held imaging system 300 to use any number of services associated with the enterprise system. The connect module 344 allows the hand-held imaging system 300 to establish an end-to-end secure, authenticated communication pipe with the host system. A subset of applications for which access is provided by the connect module 344 can be used to pass IT policy commands from the host system to the hand-held imaging system 300. This can be done in a wireless or wired manner. These instructions can then be passed to the IT policy module 346 to modify the configuration of the hand-held imaging system 300. Alternatively, in some cases, the IT policy update can also be done over a wired connection.

The IT policy module 346 receives IT policy data that encodes the IT policy. The IT policy module 346 then ensures that the IT policy data is authenticated by the hand-held imaging system 300. The IT policy data can then be stored in the RAM 306 in its native form. After the IT policy data is stored, a global notification can be sent by the IT policy module 346 to all of the applications residing on the hand-held imaging system 300. Applications for which the IT policy may be applicable then respond by reading the IT policy data to look for IT policy rules that are applicable.

The programs 337 can also include an ACL risk score generator 350. A solid-state image transducer 354 captures images 356 and the ACL risk score generator 350 generates the ACL risk score(s) 352. In some implementations, the ACL risk score(s) 352 are expressed as "high risk" "low risk", or "red light" "green light". In one implementation, the solid-state image transducer 354 records 4-5 seconds of imagery, at 120 hz (roughly 60 frames per second), which is 60-75 frames of useful information. In some implementations, the hand-held imaging system 300 includes the solid-state image transducer 354 in an internal or external camera module that performs the functions of the motion sensing input device 102.

The ACL risk score generator 350 performs substantially similar functions in FIG. 1 as the instructions 120 that the processor 114 can perform to analyze motion of the subject 106, angle of the knee joint of the subject, jumping and landing mechanics of the subject 106, balance of the subject 106 in reference to the skeletal tracking and calculating joint angles at different time points, and to determine the potential injury to the knee anterior cruciate ligament of the subject 106, that generates the determination of potential injury 122 to a knee anterior cruciate ligament of a subject 118. Additional variables such as biological gender of the subject 106 (male vs female), sport(s) played by the subject 106, and/or previous injury(ies) of the subject 106 can also be input. The ACL risk score generator 350 performs substantially similar functions in FIG. 2 as the instructions 214 that the processor 208 can perform to analyze motion of the subject 106, angle of the knee joint of the subject, jumping and landing mechanics of the subject 106, balance of the subject 106 in reference to the skeletal tracking and calculating joint angles at different time points, and to determine the potential injury to the knee anterior cruciate ligament of the subject 106, that generates a determination 216 of potential injury to a knee anterior cruciate ligament of the subject 106. Additional variables such as biological gender of the subject 106 (male vs female), sport(s) played by the subject 106, and/or previous injury(ies) of the subject 106 can also be input.

In some implementations, the ACL risk score generator 350 performs the same functions as instructions that the main processor 302 can perform to analyze motion of the subject 106, angle of the knee joint of the subject, jumping and landing mechanics of the subject 106, balance of the subject 106 in reference to the skeletal tracking and calculating joint angles at different time points—to determine the potential injury to the knee anterior cruciate ligament of the subject 106 from the images 356 received from motion sensory solid state image transducer 354. Additional variables such as biological gender of the subject 106 (male vs female), sport(s) played by the subject 106, and/or previous injury(ies) of the subject 106 can also be input. In some implementations, the hand-held imaging system 300 includes no ACL risk score generator 350 and the determined ACL risk scores are received through the data port 314, the communication subsystem 304 or the short-range communications subsystem 322 from another electronic device such as the computer 112 in FIG. 1 or computer 206 in FIG. 2.

In some implementations, the ACL risk score generator 350 performs machine learning in the determination of the potential injury to the knee anterior cruciate ligament of the subject 106 as more and more sets of images 356 are processed. Machine learning in FIG. 3 uses algorithms and statistical models to perform the functions of the ACL risk score generator 350, relying on patterns and inference instead. The machine learning algorithms build a mathematical model based on sample data, known as "training data". Machine learning tasks are classified into several broad categories. In supervised machine learning, the algorithm builds a mathematical model from a set of data that contains both the inputs and the desired outputs. For example, if the task were determining whether an image contained a certain object, the training data for a supervised machine learning algorithm would include images with and without that object (the input), and each image would have a label (the output) designating whether it contained the object. In special cases, the input may be only partially available, or restricted to special feedback. Semi-supervised machine learning algorithms develop mathematical models from incomplete training data, where a portion of the sample input doesn't have labels. Classification algorithms and regression algorithms are types of supervised machine learning. Classification algorithms are used when the outputs are restricted to a limited set of values. For a classification algorithm that filters emails, the input would be an incoming email, and the output would be the name of the folder in which to file the email. For an algorithm that identifies spam emails, the output would be the prediction of either "spam" or "not spam", represented by the Boolean values true and false. Regression algorithms are named for their continuous outputs, meaning they may have any value within a range. Examples of a continuous value are the temperature, length, or price of an object. In unsupervised machine learning, the algorithm builds a mathematical model from a set of data which contains only inputs and no desired output labels. Unsupervised machine learning algorithms are used to find structure in the data, like grouping or clustering of data points. Unsupervised machine learning can discover patterns in the data, and can group the inputs into categories, as in feature machine learning. Dimensionality reduction is the process of reducing the number of "features", or inputs, in a set of data. Active machine learning algorithms access the desired outputs (training labels) for a limited set of inputs based on a budget, and optimize the choice of inputs for which it will acquire training labels. When used interactively, these can be presented to a human user for labeling. Reinforcement machine learning algorithms are given feedback in the form of positive or negative reinforcement in a dynamic environment, and are used in autonomous vehicles or in machine learning to play a game against a human opponent. Other specialized algorithms in machine learning include topic modeling, where the ACL risk score generator 350 is given a set of natural language documents and finds other documents that cover similar topics. Machine learning algorithms can be used to find the unobservable probability density function in density estimation problems. Meta machine learning algorithms learn their own inductive bias based on previous experience. In developmental robotics, robot machine learning algorithms generate their own sequences of machine learning experiences, also known as a curriculum, to cumulatively acquire new skills through self-guided exploration and social interaction with humans. These robots use guidance mechanisms such as active machine learning, maturation, motor synergies, and imitation.

An ACL risk score 352 is generated by the ACL risk score generator 354, or is received from an external source, is then displayed by display 310 or transmitted by the communication subsystem 304 or the short-range communications subsystem 322, enunciated by the speaker 318 or stored by the flash memory 308.

Other types of modules can also be installed on the hand-held imaging system 300. These modules can be third party modules, which are added after the manufacture of the hand-held imaging system 300. Examples of third party applications include games, calculators, utilities, and additional imaging devices, etc.

The additional applications can be loaded onto the hand-held imaging system 300 through of the wireless network 305, the auxiliary I/O subsystem 312, the data port 314, the short-range communications subsystem 322, or any other suitable device subsystem 324. This flexibility in application installation increases the functionality of the hand-held imaging system 300 and may provide enhanced on-device functions, communication-related functions, or both. For example, secure communication applications enable electronic commerce functions and other such financial transactions to be performed using the hand-held imaging system 300.

The data port 314 enables a subscriber to set preferences through an external device or module and extends the capabilities of the hand-held imaging system 300 by providing for information or module downloads to the hand-held imaging system 300 other than through a wireless communication network. The alternate download path may, for example, be used to load an encryption key onto the hand-held imaging system 300 through a direct and thus reliable and trusted connection to provide secure device communication.

The data port 314 can be any suitable port that enables data communication between the hand-held imaging system 300 and another computing device. The data port 314 can be a serial or a parallel port. In some instances, the data port 314 can be a USB port that includes data lines for data transfer and a supply line that can provide a charging current to charge the battery 330 of the hand-held imaging system 300.

The short-range communications subsystem 322 provides for communication between the hand-held imaging system 300 and different systems or devices, without the use of the wireless network 305. For example, the short-range communications subsystem 322 may include a motion sensory device and associated circuits and modules for short-range communication. Examples of short-range communication standards include standards developed by the Infrared Data Association (IrDA), Bluetooth®, and the 802.11 family of standards developed by IEEE. In other implementations, Zigbee® or Z-Wave® can be used instead of Bluetooth®.

Bluetooth® is a wireless technology standard for exchanging data over short distances (using short-wavelength radio transmissions in the ISM band from 2400-2480 MHz) from fixed and mobile devices, creating personal area networks (PANs) with high levels of security. Created by telecom vendor Ericsson in 1994, Bluetooth® was originally conceived as a wireless alternative to RS-232 data cables. Bluetooth® can connect several devices, overcoming problems of synchronization. Bluetooth® operates in the range of 2400-2483.5 MHz (including guard bands), which is in the globally unlicensed Industrial, Scientific and Medical (ISM) 2.4 GHz short-range radio frequency band. Bluetooth® uses a radio technology called frequency-hopping spread spectrum. The transmitted data is divided into packets and each packet is transmitted on one of the 79 designated Bluetooth® channels. Each channel has a bandwidth of 1 MHz. The first channel starts at 2402 MHz and continues up to 2480 MHz in 1 MHz steps. The first channel usually performs 1600 hops per second, with Adaptive Frequency-Hopping (AFH) enabled. Originally Gaussian frequency-shift keying (GFSK) modulation was the only modulation scheme available; subsequently, since the introduction of Bluetooth® 2.0+EDR, π/4-DQPSK and 8DPSK modulation may also be used between compatible devices. Devices functioning with GFSK are said to be operating in basic rate (BR) mode where an instantaneous data rate of 1 Mbit/s is possible. The Bluetooth® Core Specification provides for the connection of two or more piconets to form a scatternet, in which certain devices simultaneously play the master role in one piconet and the slave role in another. At any given time, data can be transferred between the master and one other device (except for the little-used broadcast mode. The master chooses which slave device to address; typically, the master switches rapidly from one device to another in a round-robin fashion. Since the master chooses which slave to address, whereas a slave is (in theory) supposed to listen in each receive slot, being a master is a lighter burden than being a slave. Being a master of seven slaves is possible; being a slave of more than one master is difficult. Many of the services offered over Bluetooth® can expose private data or allow the connecting party to control the Bluetooth® device. For security reasons it is necessary to be able to recognize specific devices and thus enable control over which devices are allowed to connect to a given Bluetooth® device. At the same time, it is useful for Bluetooth® devices to be able to establish a connection without user intervention (for example, as soon as the Bluetooth® devices of each other are in range). To resolve this conflict, Bluetooth® uses a process called bonding, and a bond is created through a process called pairing. The pairing process is triggered either by a specific request from a user to create a bond (for example, the user explicitly requests to "Add a Bluetooth® device"), or the pairing process is triggered automatically when connecting to a service where (for the first time) the identity of a device is required for security purposes. These two cases are referred to as dedicated bonding and general bonding respectively. Pairing often involves some level of user interaction; this user interaction is the basis for confirming the identity of the devices.

In use, a received signal such as a text message, an e-mail message, or web page download will be processed by the communication subsystem 304 and input to the main processor 302. The main processor 302 will then process the received signal for output to the display 310 or alternatively to the auxiliary I/O subsystem 312. A subscriber may also compose data items, such as e-mail messages, for example, using the keyboard 316 in conjunction with the display 310 and possibly the auxiliary I/O subsystem 312. The auxiliary I/O subsystem 312 may include devices such as: a touch screen, mouse, track ball, infrared fingerprint detector, or a roller wheel with dynamic button pressing capability. The keyboard 316 is preferably an alphanumeric keyboard and/or telephone-type keypad. However, other types of keyboards may also be used. A composed item may be transmitted over the wireless network 305 through the communication subsystem 304.

For voice communications, the overall operation of the hand-held imaging system 300 is substantially similar, except that the received signals are output to the speaker 318, and signals for transmission are generated by the microphone 320. Alternative voice or audio I/O subsystems, such as a voice message recording subsystem, can also be implemented on the hand-held imaging system 300. Although voice or audio signal output is accomplished primarily through the speaker 318, the display 310 can also be used to provide additional information such as the identity of a calling party, duration of a voice call, or other voice call related information.

Method Implementations

In the previous section, apparatus of the operation of an implementation was described. In this section, the particular methods performed by processor 114 in FIG. 1, processor 208 in FIG. 2, main processor 302 in FIG. 3 and processing unit 604 in FIG. 6 of such an implementation are described by reference to a flowchart.

FIG. 4 is a flowchart of a method 400 to determine potential of injury to the ACL of a subject (expressed as a ACL risk score) from motion sensory images of a knee of the subject, according to an implementation.

Method 400 is one implementation of the process performed by the instructions 120 in FIG. 1, instructions 214 in FIG. 2 and the ACL risk score generator 350 in FIG. 3.

Method 400 includes skeletal tracking and calculating joint angles at different time points 402 between the ACL images and known angles of the knee that are associated with increased risk of ACL injury. Examples of the ACL images are motion sensory image 110 in FIG. 1, motion sensory image 204 in FIG. 2 and images 356 in FIG. 3.

Method 400 also includes analyzing 404 a motion of the subject in the images, analyzing the angle of the joints, trunk and lower extremities of the subject, analyzing jumping and landing mechanics of the subject, analyzing balance of the subject the results of the skeletal tracking and calculating joint angles at different time points.

Method 400 also includes determining 406 a potential injury to the ACL of the subject 106, which in some implementations is performed as (measured angle−uninjured angle)/(injured angle−uninjured angle).

In some implementations, method 400 is implemented as a sequence of computer instructions which, when executed by a processor (such as processor 114 in FIG. 1, processor 208 in FIG. 2, main processor 302 in FIG. 3 and processor 604 in FIG. 6), cause the processor to perform the respective method. In other implementations, method 400 is implemented as a computer-accessible medium having executable instructions capable of directing a processor, such as processor 604 in FIG. 6, to perform the respective method. In varying implementations, the medium is a magnetic medium, an electronic medium, or an optical medium.

While method 400 is not limited to any particular knee ACL, subject, imaging apparatus or processor; for sake of clarity; a simplified knee ACL, subject, imaging apparatus and processor are described.

Hardware and Operating Environment

Figure 5:
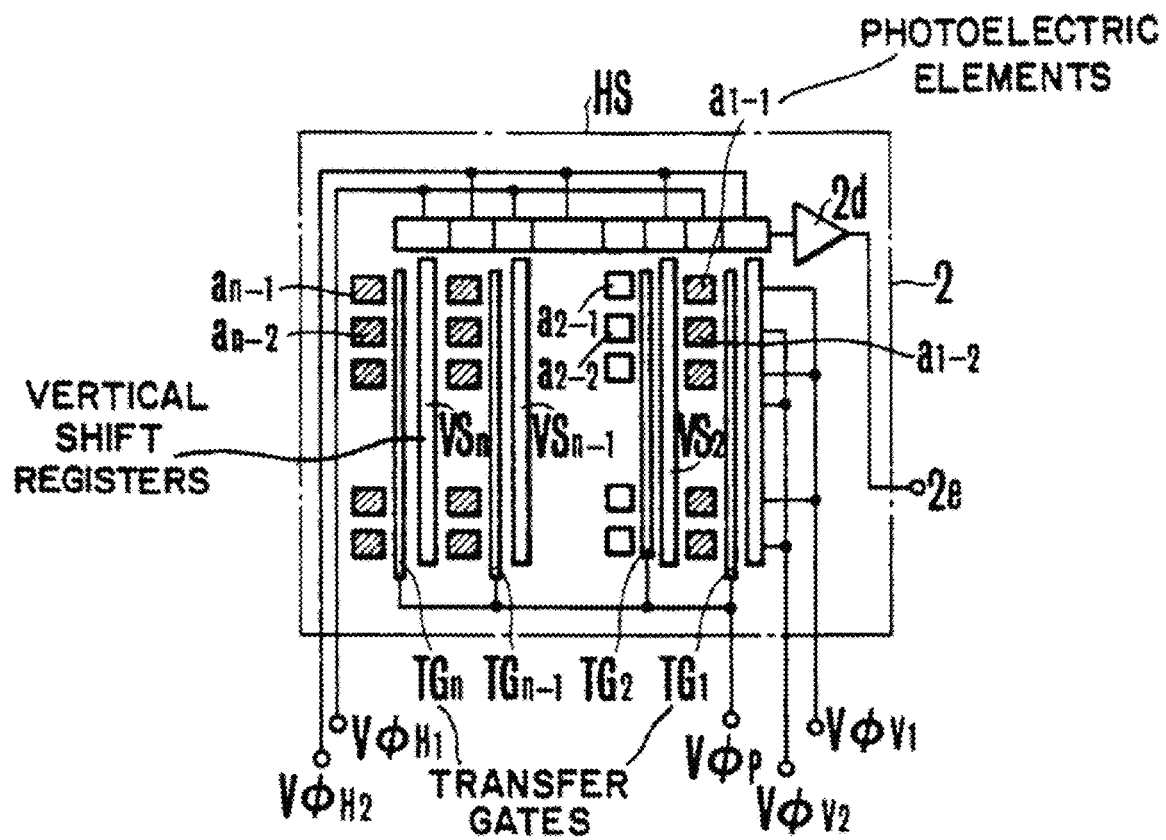
FIG. 5 is a block diagram of a solid-state image transducer, according to an implementation.

FIG. 5 is a block diagram of a solid-state image transducer 500, according to an implementation. The solid-state image transducer 500 is one component of the motion sensing input device 102. The solid-state image transducer 500 is one component of the 3D video recording input device 202 in a Microsoft Kinect for Xbox One. The solid-state image transducer 500 is one example of the solid-state image transducer 354. The solid-state image transducer 500 includes a great number of photoelectric elements, $a_{1 \ldots}$ sub.1, $a_{.sub.2} \ldots$ sub.1, ..., a.sub.mn, in the minute segment form, transfer gates TG1, TG2, ..., TGn responsive to a control pulse V.sub.φP for transferring the charges stored on the individual photoelectric elements as an image signal to vertical shift registers VS1, VS2, . . . , VSn, and a horizontal shift register HS for transferring the image signal from the vertical shift registers VSs, through a buffer amplifier to an outlet. After the one-frame image signal is stored, the image signal is transferred to vertical shift register by the pulse V.sub.φP and the contents of the vertical shift registers VSs are transferred upward line by line in response to a series of control pulses V.sub.φV1, V.sub.φV2. During the time interval between the successive two vertical transfer control pulses, the horizontal shift register HS responsive to a series of control pulses V.sub.φH1, V.sub.φH2 transfers the contents of the horizontal shift registers HSs in each line row by row to the right as viewed in FIG. 5. As a result, the one-frame image signal is formed by reading out the outputs of the individual photoelectric elements in such order.

FIG. 6 is a block diagram of a hardware and operating environment 600 in which different implementations can be practiced. The description of FIG. 6 provides an overview of computer hardware and a suitable computing environment in conjunction with which some implementations can be implemented. Implementations are described in terms of a computer executing computer-executable instructions. However, some implementations can be implemented entirely in computer hardware in which the computer-executable instructions are implemented in read-only memory. Some implementations can also be implemented in client/server computing environments where remote devices that perform tasks are linked through a communications network. Program modules can be located in both local and remote memory storage devices in a distributed computing environment.

Computer 602 includes a processor 604, commercially available from Intel, Motorola, Cyrix and others. The computer 602 is one implementation of computer 112 in FIG. 1 and computer 206 in FIG. 2. The processor 604 is one example of processor 114 in FIG. 1 and processor 208 in FIG. 2. The computer 602 also includes system memory 606 that includes random-access memory (RAM) 608 and read-only memory (ROM) 610. The RAM 608 and the ROM 610 are examples of the memory 116 in FIG. 1 and memory 210 in FIG. 2. The computer 602 also includes one or more mass storage devices 612; and a system bus 614 that operatively couples various system components to the processing unit 604. The memory 608 and 610, and mass storage devices 612, are types of computer-accessible media. Mass storage devices 612 are more specifically types of nonvolatile computer-accessible media and can include one or more hard disk drives, floppy disk drives, optical disk drives, and tape cartridge drives. The processor 604 executes computer programs stored on the computer-accessible media.

Computer 602 can be communicatively connected to the Internet 616 via a communication device, such as modem 618. Internet 616 connectivity is well known within the art. In one implementation, the modem 618 responds to communication drivers to connect to the Internet 616 via what is known in the art as a "dial-up connection." In another implementation, the communication device is an Ethernet® or network adapter 620 connected to a local-area network (LAN) 622 that itself is connected to the Internet 616 via what is known in the art as a "direct connection" (e.g., T1 line, etc.).

A user enters commands and information into the computer 602 through input devices such as a keyboard (not shown) or a pointing device (not shown). The keyboard permits entry of textual information into computer 602, as known within the art, and implementations are not limited to any particular type of keyboard. Pointing device permits the control of the screen pointer provided by a graphical user interface (GUI) of operating systems such as versions of Microsoft Windows®. Implementations are not limited to any particular pointing device. Such pointing devices include mice, touch pads, trackballs, remote controls and point sticks. Other input devices (not shown) can include a microphone, joystick, game pad, satellite dish, scanner, or the like.

In some implementations, computer 602 is operatively coupled to a display device 624. Display device 624 is connected to the system bus 614 through a video adapter 626. Display device 624 permits the display of information, including computer, video and other information, for viewing by a user of the computer. Implementations are not limited to any particular display device 624. Such display devices include cathode ray tube (CRT) displays (monitors), as well as flat panel displays such as liquid crystal displays (LCD's). In addition to a monitor, computers typically include other peripheral input/output devices such as printers (not shown). Speakers (not shown) provide audio output of signals. Speakers are also connected to the system bus 614.

Computer 602 can be operated using at least one operating system to provide a graphical user interface (GUI) including a user-controllable pointer. Computer 602 can have at least one web browser application program executing within at least one operating system, to permit users of computer 602 to access intranet or Internet world-wide-web pages as addressed by Universal Resource Locator (URL) addresses. Examples of browser application programs include Netscape Navigator® and Microsoft Internet Explorer®.

The computer 602 can operate in a networked environment using logical connections to one or more remote computers, such as remote computer 628. These logical connections are achieved by a communication device coupled to, or a part of, the computer 602. Implementations are not limited to a particular type of communications device. The remote computer 628 can be another computer, a server, a router, a network PC, a client, a peer device or other common network node. The logical connections depicted in FIG. 6 include the local-area network (LAN) 622 and a wide-area network (WAN). Such networking environments are commonplace in offices, enterprise-wide computer networks, intranets and the Internet.

When used in a LAN-networking environment, the computer 602 and remote computer 628 are connected to the local network 622 through network interfaces or adapters 620, which is one type of communications device 618. When used in a conventional WAN-networking environment, the computer 602 and remote computer 628 communicate with a WAN through modems. The modems, which can be internal or external, is connected to the system bus 614. In a networked environment, program modules depicted relative to the computer 602, or portions thereof, can be stored in the remote computer 628.

Computer 602 also includes an operating system 630 that can be stored on the RAM 608 and ROM 610, and mass storage device 612, and is and executed by the processor 604. Examples of operating systems include Microsoft Windows®, Apple MacOS®, Linux®, UNIX®, providing capability for supporting application programs 632 using, for example, code modules written in the C++® computer programming language. Examples are not limited to any particular operating system, however, and the construction and use of such operating systems are well known within the art.

Instructions can be stored via the mass storage devices 612 or system memory 606, including one or more application programs 632, other program modules 634 and program data 636.

Computer 602 also includes power supply. Each power supply can be a battery.

Some implementations include computer instructions to generate and operate a patient input screen that can be implemented in instructions 120 in FIG. 1, instructions 214 in FIG. 2, or the ACL risk score generator 350 in FIG. 3 or the instructions stored via the mass storage devices 612 or system memory 606 in FIG. 6.

Some implementations include computer instructions to generate and operate the input capture device selection screen 800 that can be implemented in instructions 120 in FIG. 1, instructions 214 in FIG. 2, or the ACL risk score generator 350 in FIG. 3 or the instructions stored via the mass storage devices 612 or system memory 606 in FIG. 6.

Some implementations include computer instructions to generate and operate an analysis module jump type selection screen, a recordation initiation screen, a playback window screen, and a jump data and prediction screen that can be implemented in instructions 120 in FIG. 1, instructions 214 in FIG. 2, or the ACL risk score generator 350 in FIG. 3 or the instructions stored via the mass storage devices 612 or system memory 606 in FIG. 6.

CONCLUSION

An ACL injury risk determination system is described herein. A technical effect of the ACL injury risk determination system is determination of potential injury to the ACL of a subject (in some implementations expressed as a ACL risk score) from motion sensory images of a knee of the subject. Although specific implementations are illustrated and described herein, it will be appreciated by those of ordinary skill in the art that any arrangement which is calculated to achieve the same purpose may be substituted for the specific implementations shown. This application is intended to cover any adaptations or variations. For example, although described in general terms, one of ordinary skill in the art will appreciate that implementations can be made using any other imaging technology that provides the required function.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations. One of skill in the art will readily recognize that implementations are applicable to future imaging devices, different processors, and new gait analyses, angle of knee joint analyses, jumping/landing mechanics analyses, balance analyses of the subject, biological gender of the subject (male vs female), sport(s) played by the subject, and/or previous injury(ies) of the subject.

The terminology used in this application meant to include computing environments and alternate technologies which provide the same functionality as described herein.

The invention claimed is:

1. A computer-based system for determining a prediction of future injury to a knee anterior cruciate ligament of a subject, the computer-based system comprising:
 a motion sensing input device generating a plurality of images of the subject, the subject having no markers attached to the subject, the motion sensing input device having photoelectric elements, transfer gates that are responsive to a control pulse for transferring the charges stored on the individual photoelectric elements as an image signal to vertical shift registers and a horizontal shift register for transferring an image signal from the vertical shift registers through a buffer amplifier to an outlet, the plurality of images being captured at least 30 frames per second, each of the plurality of images having a resolution of at least 640×480 pixels and 10 bit depth, having at least 2,048 levels of sensitivity;
 a computer having a processor, a memory and input/output capability, the processor being configured to perform:
 a pose recognition or a skeletal tracking and calculating of joint angles at different time points;
 the processor being further configured to analyze from the plurality of images a motion of the subject, an angle of the knee joint of the subject, jumping and landing mechanics of the subject, and a balance of the subject in reference to either the pose recognition, or the skeletal tracking and calculating of the joint angles at the different time points
 the processor being then further configured to determine the prediction of future injury to the knee anterior cruciate ligament of the subject based on the analysis of the plurality of images, wherein the prediction of future injury to the knee anterior cruciate ligament of the subject further comprises an ACL risk score;
 the processor being then further configured to display the ACL risk score by a display, or transmit the ACL risk score by a communication subsystem, a transmit the ACL risk score by short-range communications subsystem, enunciate the ACL risk score by a speaker, or store the ACL risk score by a flash memory into the processor;
 the processor being then further configured to generate and operate a prediction screen displaying the ACL risk score, wherein the ACL risk score is expressed on the prediction screen as "high risk" or "low risk";
 wherein the processor is configured to determine the prediction of future injury to the knee anterior cruciate ligament by performing machine learning processes utilizing a model trained from a set of data that contains both desired inputs and desired outputs,
 in which the set of data for training the model includes images with and without the desired inputs,
 and each image includes a label for the desired output designating whether the image contained a desired training object;
 wherein the machine learning processes include supervised regression learning which produces continuous outputs, wherein the continuous outputs are a continuous range of values for the ACL risk score.

2. The computer-based system of claim 1, wherein the computer-based system does not comprise a motion profile, the motion profile further not comprising ranges of node angle value.

3. The computer-based system of claim 1, wherein the computer-based system does not comprise ranges of node angle value in a motion profile.

4. The computer-based system of claim 1, wherein the computer-based system does not comprise a motion profile, the motion profile further comprising ranges of node angle value or displacement experienced for one or more exercises.

5. The computer-based system of claim 1, wherein the computer-based system does not comprise a database of previously recorded motion profiles.

6. The computer-based system of claim 1, wherein the computer-based system does not determine a rehab/treatment schedule.

7. The computer-based system of claim 1, wherein the processor being further configured to perform the pose recognition or the skeletal tracking and the calculating joint angles at the different time points and being configured to analyze a gait of the subject, angle of the knee joint of the subject and jumping and the landing mechanics of the subject and the balance of the subject in further reference to other variables including biological gender of the subject, sport played by the subject, and/or previous injury of the subject to determine the prediction of future injury to the knee anterior cruciate ligament of the subject.

8. A computer-based system for determining a prediction of future injury to a knee anterior cruciate ligament of a subject, the computer-based system comprising:
- a motion sensing input device generating a plurality of images of the subject, the subject having no markers attached to the subject, the motion sensing input device having photoelectric elements, transfer gates that are responsive to a control pulse for transferring the charges stored on the individual photoelectric elements as an image signal to vertical shift registers and a horizontal shift register for transferring an image signal from the vertical shift registers through a buffer amplifier to an outlet, the plurality of images being captured at least 30 frames per second, each of the plurality of images having a resolution of at least 640×480 pixels and 10 bit depth and having at least 2,048 levels of sensitivity;
- a computer having a processor, a memory and input/output capability, the processor being configured to perform:
- a pose recognition or a skeletal tracking and calculating of joint angles at different time points;
- the processor being further configured to analyze from the plurality of images a motion of the subject, an angle of the knee joint of the subject, jumping and landing mechanics of the subject in reference to either the pose recognition, or the skeletal tracking and calculating of the joint angles at the different time points based on the analysis of the plurality of images;
- the processor being then further configured to determine the prediction of future injury to the knee anterior cruciate ligament of the subject based on the analysis of the plurality of images, wherein the prediction of future injury to the knee anterior cruciate ligament of the subject further comprises an ACL risk score;
- the processor being then further configured to save the ACL risk score into the memory as "at risk";
- and the processor being then further configured to generate and operate a prediction screen displaying the ACL risk score, wherein the ACL risk score is expressed on the prediction screen as "high risk" or "low risk";
- wherein the processor is configured to determine the prediction of future injury to the knee anterior cruciate ligament by performing machine learning processes utilizing a model trained from a set of data that contains both desired inputs and desired outputs,
- in which the set of data for training the model includes images with and without the desired inputs,
- and each image includes a label for the desired output designating whether the image contained a desired training object;
- wherein the machine learning processes include supervised regression learning which produces continuous outputs, wherein the continuous outputs are a continuous range of values for the ACL risk score.

9. The computer-based system of claim 8, wherein the computer-based system does not comprise ranges of node angle value in a motion profile.

10. The computer-based system of claim 8, wherein the computer-based system does not comprise a motion profile, the motion profile further comprising ranges of node angle value or displacement experienced for one or more exercises.

11. The computer-based system of claim 8, wherein the computer-based system does not comprise a database of previously recorded motion profiles.

12. The computer-based system of claim 8, wherein the computer-based system does not determine a rehab/treatment schedule.

13. The computer-based system of claim 8, wherein the processor being further configured to perform the skeletal tracking and calculating of the joint angles at the different time points and the processor then being further configured to analyze a gait of the subject, an angle of the knee joint of the subject, jumping and the landing mechanics of the subject in further reference to other variables including biological gender of the subject, sport played by the subject, and/or previous injury of the subject.

14. The computer-based system of claim 8, wherein the processor being further configured to determine the prediction of future injury to the knee anterior cruciate ligament of the subject from images captured by a hand-held imaging system.

* * * * *